United States Patent [19]

Bisconte

[11] Patent Number: 4,696,902
[45] Date of Patent: Sep. 29, 1987

[54] MODULAR APPARATUS FOR CELL CULTURE

[75] Inventor: Jean-Claude Bisconte, Paris, France

[73] Assignee: Institut National de la Sante et de la Recherche Medicale (INSERM), Paris, France

[21] Appl. No.: 742,046

[22] Filed: Jun. 6, 1985

[30] Foreign Application Priority Data

Jun. 6, 1984 [FR] France ............... 84 08839

[51] Int. Cl.⁴ ............................................. C12M 1/18
[52] U.S. Cl. ................................. 435/300; 435/313
[58] Field of Search ................ 435/287, 300, 313; 414/1, 8; 901/6

[56] References Cited

U.S. PATENT DOCUMENTS

| 3,106,090 | 10/1903 | Barnes | 435/300 X |
| 3,501,379 | 3/1970 | Tate | 435/300 X |
| 4,090,921 | 6/1978 | Sawamura et al. | |
| 4,339,537 | 7/1982 | Sogi et al. | |
| 4,442,387 | 4/1984 | Lindbom | 414/1 |

FOREIGN PATENT DOCUMENTS

| 2633085 | 1/1977 | Fed. Rep. of Germany . |
| 2945339 | 5/1980 | Fed. Rep. of Germany . |
| 157739 | 8/1969 | France . |
| 926541 | 6/1963 | United Kingdom . |
| 1112919 | 6/1968 | United Kingdom . |

Primary Examiner—Alan Cohan
Attorney, Agent, or Firm—Browdy and Neimark

[57] ABSTRACT

The present invention relates to a modular apparatus for cell culture, comprising in the same sealed enclosure (2) with isotherm walls (3):

at least one device (1, R, E) for storing culture containers, at least one temperature regulation device (7), a closed circuit filtered laminar flow sterilization device (11, 12, 13, 14), a device for supplying and regulating gas, such as air, $CO_2$, vapor and/or similar, and in that the enclosure possibly contains at least one additional device for carrying out any one of the conventional cell culture operations, or any other specific operation, and defining a modular work post chosen depending on the needs.

The apparatus may also comprise an automatic and programmable handling arm (B) and a microprocessor for controlling and processing the data.

29 Claims, 12 Drawing Figures

MODULAR APPARATUS FOR CELL CULTURE

BACKGROUND OF THE INVENTION

The present invention relates to a modular apparatus for carrying out the essential phases of cell culture and analysis using robots if necessary.

The culture of procaryote and encaryote cells is practised in laboratories and industries in the main fields hereafter:

fundamental and applied research concerning the cell mechanisms (growth, differentiation, interaction) in varied disciplines (cell biology, cancerology, hormonology, study and testing of medicaments, etc . . . );

biotechnological research and industry with a view to cell manipulation and selection (hybridome clonage, for example):

toxicological analysis of foods, effluents, dyes or others, and medical diagnosis passing through the preparation of human (cytogenetic, cancerology ) or bacterial cultures.

Cell culture is generally based on two kinds of methods, depending on the final result sought:

on the one hand, manual methods, widely used for small scale preparatory and analytic purposes, in which the main equipment hereafter is available:

thermostat controlled enclosures (with or without $CO_2$), laminarflow hoppers, culture containers formed by Petri boxes, multihole boxes or flasks, setting under culture or removal of cells or nutritive medium being carried out manually with a Pasteur pipette or, more recently, by means of semi-automatic devices with disposable plastic cones, whereas the morphological analysis generally takes place manually under an inverted microscope, on the other hand, automated methods in bioreactors which allow the mass culture of floating cells for industrial production purposes and which are not directly concerned by the present invention.

It will be recalled that the manual methods comprise the main following phases:

1. Cell sampling (by dissociation,transplantation);
2. Placing under culture.,
3. Maintaining the cultures so as to obtain more especially growth and differentiation, which requires:
   storage under defined temperature, hygrometry, 10% $CO_2$ and pH conditions,
   renewal of the nutritive medium, and
   checking for non contamination and development of the process;
4. Interaction with the cell culture, for example by addition of an appropriate product or cells;
5. Taking cells for transplantation, or taking samples of the nutritive medium with a view to quantity determination, and
6. Morphological, biochemical, physical or similar analysis of the cell culture.

Said phases actually form a sequence of dissociated operations which, in all cases, leads to momentary variations in conditions all the consequences of which it is difficult to estimate. In fact, said culture containers are caused to transit between different apparatus:

incubator for storing the culture containers, laminarflow hopper for carrying out the manipulations, microscopic observation for checking or analysis purposes, which leads at least to an increase in the risks of mutual contamination (man - culture cells) and also leads to a thermal shock which disturbs the cell metabolism.

In addition, the high number of culture containers to be maintained, the requirement of handling them as little as possible and the absence of adapted means prevent all the information contained in the cultures from being used.

To sum up, the main problems which arise with the manual methods at present used consist in:

high contamination risks with respect to cultivated cells (encaryotes especially), with respect to the personel if the cells are themselves pathogenic or if the manipulations involve dangerous agents (cancerogenic viruses, etc . . . );

need for a considerable staff force for carrying out work which is generally fastidious for the regular upkeep of the cell cultures, which results in considerable lost time due to the dispersion of the work posts and the difficulty of optimizing the operations;

high costs for specialized parts, consumable products (culture containers, nutritive media, etc . . . ) and for equipment, which should be multiplied so as to reduce the risks of contamination and so as to take into account the specialization of the application;

difficult biological working, related more particularly to the inevitable variability of human practice, to the non optimum environmental conditions (heat, mechanical and chemical shocks induced by handling), the impossibility of following and quantifying the biological processes which take place permanently in the cultures and a fbrtiori of acting retroactively thereon.

However, improvements have been made in some fields. Thus:

the incubator for storing the cultures and the laminarflow hopper have been juxtaposed by the firm HERAEUS;

numerous semi-automated devices exist for taking samples or diluting the cell medium;

constructors such as LEITZ propose microscopes contained in $CO_2$ enclosures which are simply thermostat controlled but which do not provide sterility nor the constancy of a high degree of hygrometry, which can be explained in so far as the last point is concerned by the incompatibility with the optical and electromechanical components;

Prof. J.-C. BISCONTE has already proposed a device associating cell culture with automation, real-time and continuous image analysis for following the cell interaction events (MIK-ROSKOPIE, 1980);

other solutions have been proposed, always in the direction of automation, such as those of WALKER and POZNANOVIC (International Biotechnology Laboratory, December 1983) who have constructed a multichamber device in which the conditions are programmable and which applies particulary to cells in suspension, but this device is not appropriate for:

the automated culture of a high number of samples, the use of existing commercial containers, morphological analysis, automatic clonage and so is a device very different from that provided by the present invention.

GENERAL DESCRIPTION OF THE INVENTION

The aim of the invention is therefore to overcome the drawbacks of the prior methods of cell culture, in particular in so far as the risks of mutual contamination, the investment costs and operating costs are concerned.

Another aim of the invention is to integrate all the phases relating to the cell culture and which, up to now, form a sequence of dissociated operations, while being able to use traditional culture containers which may be made reusable, without for all that excluding the use of special containers.

Another aim of the invention is to approximate optimum conditions by totally suppressing thermal as well as mechanical and chemical shocks, by making the culture conditions uniform independently of the operator.

Another aim of the invention is to make the environmental conditions of the cells, including the nutritive medium, dependent on frequently or even continuously measured parameters, using software.

The present invention provides then a modular cell culture apparatus, characterized in that it comprises, in the same sealed enclosure with isotherm walls:

at least one device for storing culture containers such as multihole boxes, flasks or similar, a temperature regulation device, a closed circuit filtered laminarflow sterilization device, a device for supplying and regulating gas, such as air, $CO_2$, vapor and/or similar, and in that said enclosure possibly comprises at least one additional device for carrying out any one of the conventional cell culture operations, or any other specific operation, and defining a modular work post chosen as a function of the needs, in addition to the modular post corresponding to said storage device.

In a preferred embodiment of the modular apparatus of the invention, the sealed enclosure also contains at least one automatic and programmable arm, which is provided with handling nippers or similar and which carries out all the operations corresponding to each of the work posts.

In an advantageous embodiment of the apparatus according to the invention, the storage device comprises a plurality of modules forming shelving provided with slides along which slide sealed compartments containing conventional culture containers and closed by lids, slightly conical, having a handle and O-seals.

In a preferred arrangement of this embodiment, the gas supply to each compartment is provided automatically by means of said handling arm, which sucks up the gas to be renewed, which allows the composition to be analyzed, and which injects the renewal gas more especially through a system of two valves formed in the handle of the lid closing each compartment and having two ducts communicating with an injection duct and a suction duct, respectively, carried by the handling arm and activated when the handle of the lid is gripped by the gripper of the arm.

In an advantageous arrangement of this embodiment, each compartment is held in position by means of a non return rod interposed between the wall of the shelving module and that of the compartment itself.

In yet another advantageous arrangement of the apparatus of the invention, each compartment is transparent and an appropriate space is formed above and below each compartment so as to introduce, using said handling arm if required, an optical device for effecting colorimetry, opacity or other measurements to be carried out.

According to another advantageous arrangement of this embodiment, the connection between adjacent shelving modules is provided by means of vertical bars, more particularly in the shape of a T, which are provided with engagement studs penetrating into corresponding housings formed inside wings projecting from the vertical rear sides of each shelving module.

In another advantageous embodiment of the apparatus according to the invention, the storage device comprises a plurality of modules forming incubators with isotherm walls and sealed compartments and comprising three main zones, namely:

a first zone disposed in the front part, assembling together the culture containers in said compartments, a second zone disposed in the median part, assembling together the connections between each compartment and the different gas supplies, and a third zone disposed in the rear part, assembling together the gas supply devices, the regulation devices and the filters.

In an advantageous arrangement of this embodiment, said compartments are provided with a flange on their front face and are applied, by bonding or similar, to a plate provided with openings disposed in vertical rows and having various dimensions, and it is also fixed by bonding more especially to the periphery of the front face of each incubator, the gas supply for each compartment being provided automatically by means of ball studs allowing the supply valves to be opened when the compartments are closed, whereas opening of these latter deactivates the supply valves.

In an advantageous procedure of this arrangement, the culture containers, more especially of the multihole type, are secured to the lids of the compartments and form special drawer boxes cooperating with said studs activating the gas supply when these special boxes are introduced into said compartments.

In another advantageous arrangement of this embodiment, said gas supply devices converge in a mixing chamber where the air content, the $CO_2$ content and the water vapor content are more especially regulated by means of regulation devices known per se, in which chamber slides a piston directing the gas mixture to the selected compartment or compartments.

In an advantageous embodiment of the apparatus according to the invention, said additional device is formed by at least one of the following devices:

an enriched nutritive medium supply and impoverish medium removal device, and/or a device for rinsing and sterilizing the containers and/or a nutritive media distribution device, and/or a device for distributing substances, particularly pharmacological substances, and/or a cell distributing device, and/or at least one observation device comprising photonic or other, particularly acoustic, optical means coupled or not to motor driven stages, as well as to an image analyzer, to a photographic apparatus or to a video tape recorder, and/or physico-chemical analysis devices, and/or transplantation devices, and/or various storage devices, and/or devices for preparing culture containers more especially by spraying with appropriate substrates, such as collagene.

In an advantageous embodiment of the apparatus according to the invention, said impoverished nutritive medium removal device consists of a suction device comprising a step by step micro-motor which actuates, through a mechanical step down system, a piston in a cylinder threaded at its lower base, about which is screwed a suction cone with tapered and bevelled end, a membrane being clamped between this cone and the base of said cylinder and being supported by an O-seal which provides the required sealing at the same time.

In an advantageous arrangement of this embodiment, the cone is connected to two ducts for the intake of fluids for rinsing and sterilizing the internal part of the cone after the suction and impoverished medium removal operation.

In an advantageous feature of this arrangement, removal of the sucked medium takes place in a well formed in the work table of said enclosure, which well also serves as housing for the suction device and is provided with a series of rings of ducts staggered and slanted in the removal direction, which are intended for external rinsing, sterilization and drying.

In an advantageous embodiment of the apparatus according to the invention, said suction device cooperates with a liquid supply device having a self closing connection made from a flexible material, more especially from elastomer, which is subjected to the laminarflow existing inside the enclosure and into which said suction cone is introduced, whereas the supply reservoir is disposed outside the enclosure and in a cold environment, injection of new or enriched liquid nutritive medium being provided by reversing the direction of rotation of said step by step motor.

In a variant of this embodiment, the enriched nutritive medium is injected by means of an injection device which is independent of said suction device and which comprises bottles containing the liquids to be injected inside a cooling block, these liquids being conveyed by one or more pipes, made more especially from elastomer, combined together in a bundle and envelopped by an isotherm sheath projecting from the base of the cooling block, the flow in each supply pipe being controlled by a sterilizable on or off valve.

In an advantageous arrangement of this variant, the end part of the bundle of pipes is provided with an anticontamination projection sheath in which is fed a permanent air jet at a low pressure which prevents the reflux of the liquid particles, this anticontamination sheath and the ends of said supply pipes being slanted so as to direct the injection liquid against the wall of said culture housings and avoid direct impact against the cells which adhere to the bottom of each housing.

In yet another preferred embodiment of the apparatus in accordance with the invention, said apparatus further comprises a microprocessor controlling all the operations, according to a protocol of conventional experiments or experiments specially defined depending on the needs, and which also ensures possible processing of the data.

Besides the preceding arrangements, the invention comprises further arrangements which will be clear from the following description.

The invention will be better understood from the complement of description which follows with reference to the according drawings in which:

DESCRIPTION OF PREFERRED EMBODIMENT

Figure 1:
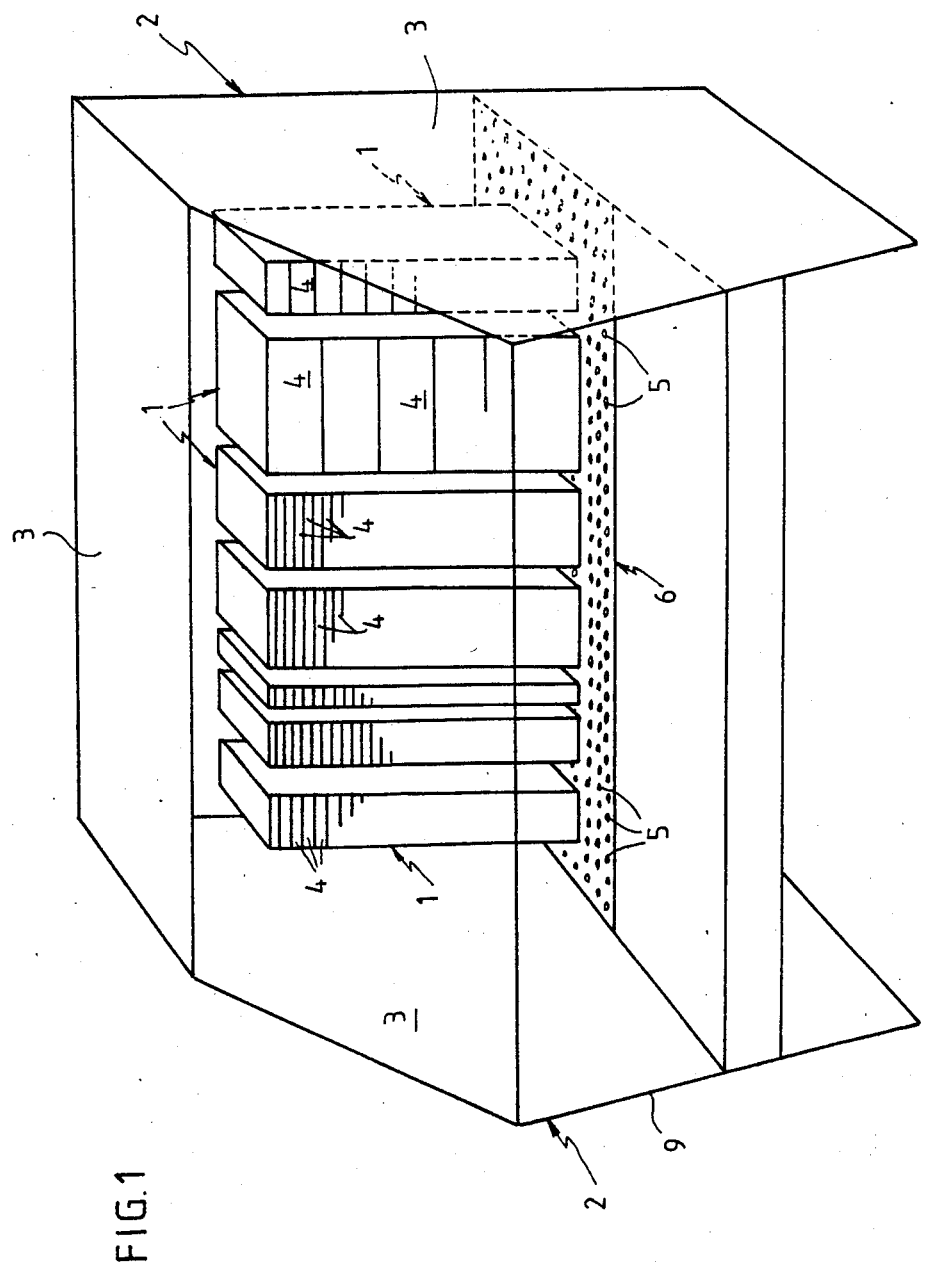
FIG. 1 is a schematical perspective view which shows one embodiment of the enclosure of the modular apparatus of the invention, in which are shown several devices for storing cell cultures in accordance with the invention (for the sake of simplicity the heat regulation, sterilization and gas supply devices have not been shown as well as the different additional devices for enriching the enclosure and forming as many modular work posts known per se)

It should of course be understood that these drawings and the corresponding descriptive parts are given solely by way of illustration of the subject of the invention, of which they form in no wise a limitation. The storage devices 1, shown schematically in FIG. 1 and contained in an enclosure 2 whose isotherm walls 3 are made preferably from a metal or plastic material, more especially transparent on the front face, contain culture containers 4 of different dimensions.

Figure 2:
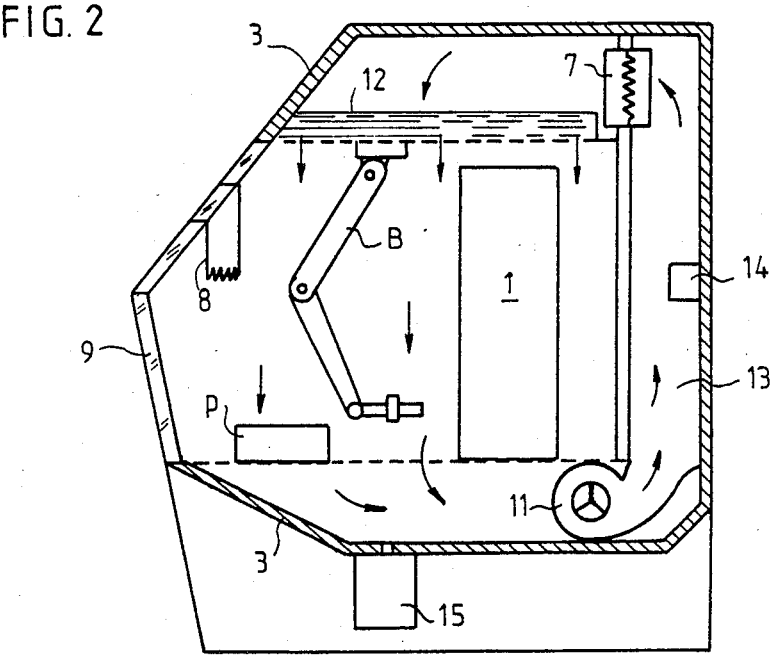
FIG. 2 is a schematical cross sectional view of the modular apparatus of the invention which shows in particular the devices for the heat regulation and sterilization of the laminarflow, more especially vertical, which are not shown in FIG. 1, as well as an automatic handling arm which may also equip the enclosure.

The assembly of the modular work posts which, as described above, may possibly enrich the enclosure 2, besides said storage devices 1, as the needs increase, is subjected to a closed circuit sterile laminarflow which is preferably downgoing (but which could also be upgoing or horizontal), which is taken up by the perforations 5 in the work table 6 and which is heated and regulated by the resistance block 7 (cf. FIG. 2). The heat losses are reduced by the isotherm walls 3, including the front face of the apparatus which is formed for example as a double glass or plastic material wall. In normal operation, the enclosure 2 is sealed and manual access is provided through passages equipped with rubber gloves 8. For carrying out manipulations, the glassed panel 9 may also be opened or an introduction air lock (not shown in FIG. 2) may be used. The hot air flow thus guarantees homogeneous heat conditions in all the containers, but also on the work plate 6. A centrifugal turbine 11 provides circulation of the gases. Sterility is ensured by the filter box 12.

Thus, the whole of the storage devices 1 is bathed in a non turbulent sterile flow which tends to eliminate, in a way known per se, possible contamination germs. An ultraviolet radiation sterilizing device 14 may further be included in the laminarflow sterilization circuit, and very advantageously in the upgoing circuit 13.

FIG. 2 also shows a handling arm B which may possibly equip the enclosure 2 and which is preferably of the anthropomorphic type, but which may also be of the linear movement and rotation type.

Figure 4:
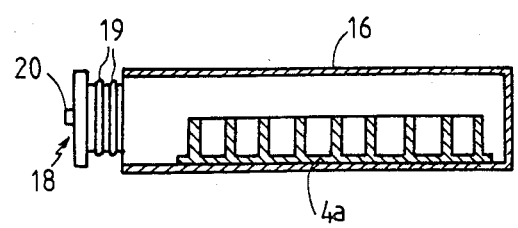
FIG. 4 shows a longitudinal sectional view of a sealed compartment which may be slid into the storage device shown in FIG. 3 and which contains more especially a culture box and the lid providing sealing, in accordance with the invention.

In normal operation, when a culture container 4 is opened, all the others are closed, which considerably limits the risks of contamination diffusion. Furthermore, accidental diffusion of the liquid nutritive medium (which may possibly contain cells), in a work post P, cannot lead to the diffusion of contamination which would result therefrom, because a device 15 for collecting liquids accidently spilled on the work plate is associated with each post P. Alternately, a single funnel shaped device (not shown) may be used placed below the table and having a lateral orifice for communicating with circuit 13. FIG. 4 shows culture containers, formed in particular by multihole boxes 4a, which are introduced in compartment 16 formed very simply by front opening boxes formed by molding, for example from a transparent plastic material such as the one used for the containers themselves.

Figure 3:
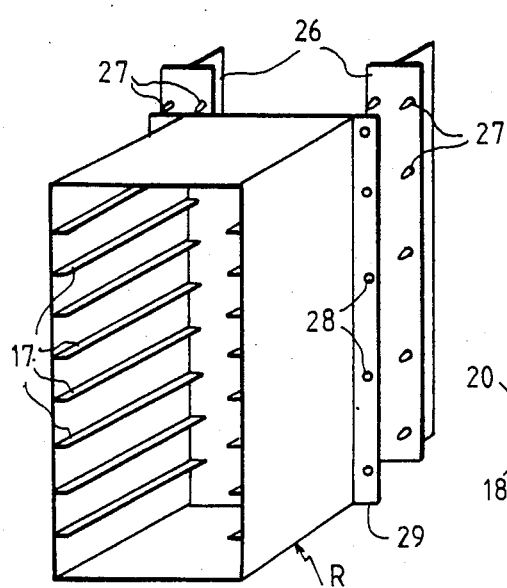
FIG. 3 shows a perspective view of one embodiment of the culture container storage device according to the invention.

These boxes 16 are stacked and bonded, or simply placed, in a storage device formed for example by simple shelving R made from metal (or from a plastic material) which is in the form of a parallelepipedic box open on the front face and on the rear face and comprising slides 17 (cf. FIG. 3). Its dimensions depend on the size of the compartments 16. These latter (cf. FIG. 4) comprise a lid equipped with O-seals 19. This lid is slightly conical and has a handle 20 for facilitating introduction thereof by hand or by said automatic handling arm B.

Figure 5:
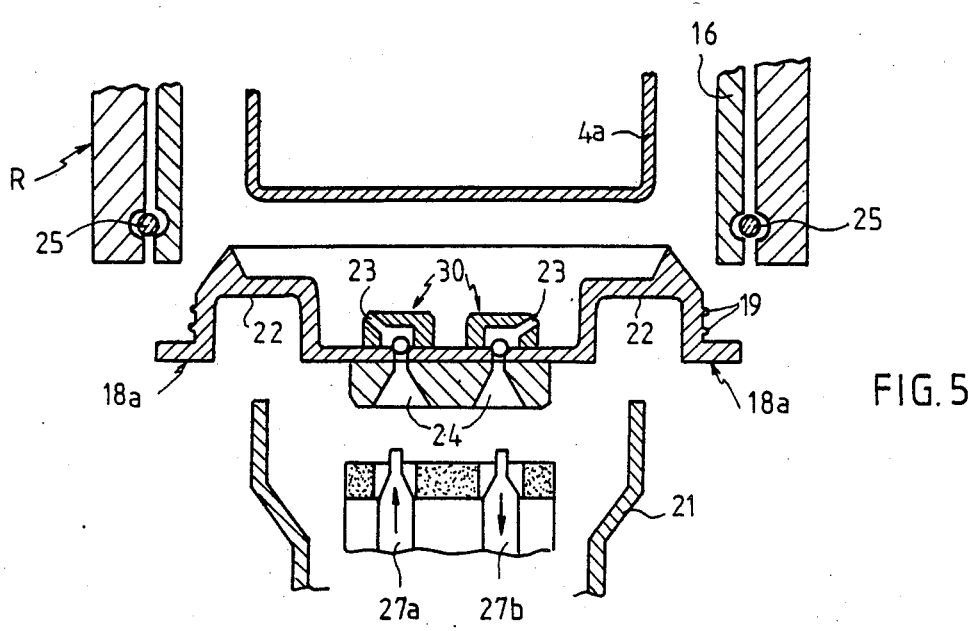
FIG. 5 shows the details of a lid associated with the compartments of FIG. 4 for cooperating with the gripper of an automatic and programmable handling arm.

If adjustment of the pH is not necessary, for example because of the use of a neutralized medium, the lid of the compartment is a simple plug 18. In the opposite case (which is at the present time the general case in encaryote culture), the lid is of a special type (cf. reference 18a in FIG. 5) for allowing recycling of the pH which is obtained by injection of an air $+CO_2$ mixture (with a few % of $CO_2$). In this case (cf. FIG. 5), the gripper 21 of the handling arm B has a movement path which allows it to grip not only the culture containers 4a but also lids 18a, these latter being recessed and having front notches 22 (cf. FIG. 5). In FIG. 5, the lids 18a are provided with a system having two valves 30 whose external orifices 24 are conical, the internal orifices 23 being orientated so as to provide efficient gas scavenging in the compartment, after introduction of the injector and the aspirator 27a, 27b, fixed to gripper 21 in the external orifices 24. At the end of travel valves 30 are open.

Depending on the program and the result of the measurement, $CO_2$ is added alone or with any other gas required (water vapor, nitrogen, etc . . . ) from a gas filtered supply device (injection and suction or aspiration being controlled by a microprocessor which further controls all the operations according to the protocol of predefined conventional experiments). Thus, without opening the lids, it is possible to check and regulate each of the boxes as often as required, the complete cycle which comprises the connection, suction, measurement and injection taking only a few seconds. Moreover, the volume of the compartment forms a sufficient gas reserve, with respect to cell consumption, for limiting the needs to a few cycles per day for each of the compartments. When it is required to remove the culture container 4a from the compartment 16, for example for changing the medium, the gripper 21 is brought by the handling arm B in a position X-Y-Z defined by the program. The gripper 21 is engaged in the lid 18a, then tightened on the side faces of said front notches 22. By a withdrawing movement of gripper 21 lid 18a is removed, then placed in an empty housing in the storage device specially reserved for this use. Gripper 21 comes back into position and penetrates into compartment 16, grips the multihole box 4a (which, it will be remembered, has neither lid nor plug and which may be replaced, either by a bottle, or by Petri boxes), exerts a withdrawal movement and places the container 4a in the corresponding work post. After the operation has been carried out, the cycle runs in the reverse direction and ends by a special gas injection for driving the gas from the enclosure which infiltrated therein during opening of the compartment. The compartments 16 are rigidly fixed by a non return rod 25, which is interposed between the wall of the storage device R and the wall of each compartment 16 while sliding in grooves formed in these walls (cf. FIG. 5).

Said shelving R engages with the vertical bars 26 (cf. FIG. 3) which are provided with studs 27 penetrating into corresponding housings 28 formed in side wings 29 projecting from the rear vertical sides of each shelving. Fixing is provided by means of a conventional snap fit system of the Zeus type for example. When the storage device 1 is formed by bonding compartments 16 together, a perforated plate is bonded to the rear face of the open box R.

For obtaining a good seating of the storage devices R, they are provided with lower feet (not shown) and possibly upper feet if their size justifies it.

It should be mentioned in passing that, since the containers containing the cells may be formed not only by multihole boxes 4a or bottles, but also by Petri boxes, it goes without saying that in this latter case a special support must be used: anyway, in each case evaporation is very low in the sealed compartment 16.

Figure 6:
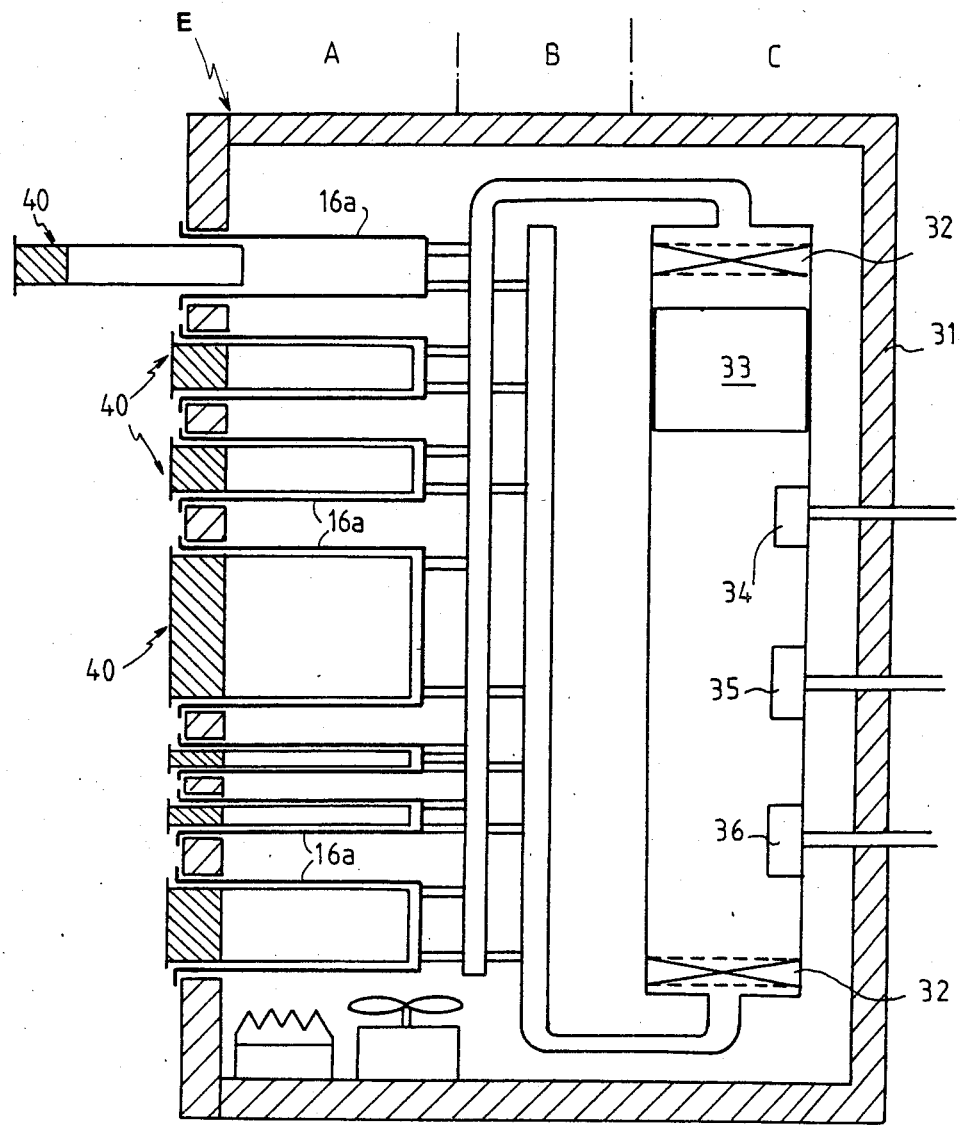

A modified form of storage device is provided by a sealed incubator E with compartments 16a shown schematically in FIG. 6 and comprising three main zones:

a front face zone A which assembles together the culture containers and which may be advantageously modular so as to accommodate various culture container formats;

an intermediate zone B assembling together the connections from compartments 16a to the different supplies, and a zone C, disposed in the rear part, comprising the gas generator, the regulation devices and the filters.

Figure 7:
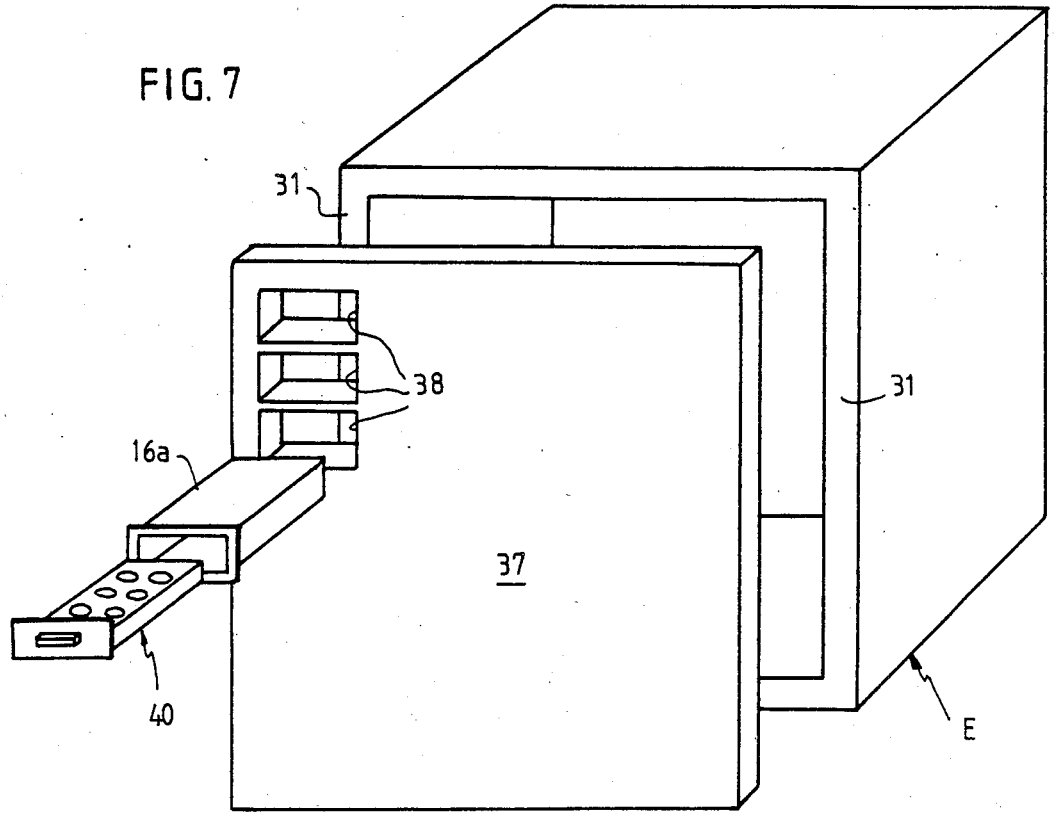
FIGS. 6 and 7 refer to another embodiment of said storage device and to a variant of the culture containers which may be supplied with gas from the rear part instead of from the front part.

In this zone C, within the isotherm thermostatically controlled walls 31, can be seen an assembly of filters 32, a pump for forcing the circulation by means of a piston 33 sliding in a mixing chamber where the air content, $CO_2$ and water content is regulated by means of conventional devices 34, 35, 36, shown schematically. Compartments 16a are connected to two groups of pipes ensuring respectively the supply and discharge. Compartments 16a, shown in FIG. 7, are made from metal or from a molded plastic material and are bonded to the front isotherm panel 37 which has been recessed by die stamping 38 to dimensions adapted to the culture containers. The front panel 37 is itself sealingly bonded to the periphery of the front face defined by cooperation of the walls of incubator E.

Compartments 16a, in comparison with the compartments 16 described above and shown in FIG. 5, have a flange on the front periphery for bonding more especially to panel 37 and may contain conventional multihole boxes: in this case, the lids are also identical to those described above. Special boxes such as shown in FIG. 7 may be advantageously used which combine a sealed and isotherm lid and which are in the form of drawer boxes 40. Each special box 40 is then introduced by hand, or by the handling arm, into compartments 16a and sealing is also provided by an O-seal.

The gas supply may be provided through the front face and using the handling arm, as described above. With a continuous gas supply, opening and closing of the gas circuits is initiated by engagement of box 40 and conversely, for example by means of a ball device which also provides mechanical closure.

Since one of the main aims of the invention is to automate the operations for removing and injecting liquid media or else cells, commercial devices exist which may be validly used, in particular those using disposable cones. The choice between a reusable device or another one using consumable components depends directly on the through-put rate of the system.

With a high number of culture containers, for example of the order of 120 boxes with 96 holes or housings each one, several thousand cones may be consumed per day. The reusable device may without difficulty treat this assembly of more than 10,000 housings in a day at the rate of a mean cycle of six seconds comprising suction of the impoverished medium, emptying, rinsing, sterilizing and filling with fresh medium. However, if the work rate so requires, it is possible to dispose several suction devices in parallel. The suction device proposed and shown in FIGS. 8 and 9 approximates to a piston system. It comprises a step by step micromotor 41 actuating a piston 42 in a cylinder 43 through a mechanical step down system. A suction cone 44 made from metal, stainless steel, aluminium, glass or even plastic (teflon), is screwed on cylinder 43. A membrane 45 is clamped between cone 44 and the base of cylinder 43. A metal or plastic material O-seal 46 faciliates fitting of membrane 45, while providing the required seal.

Figure 10:
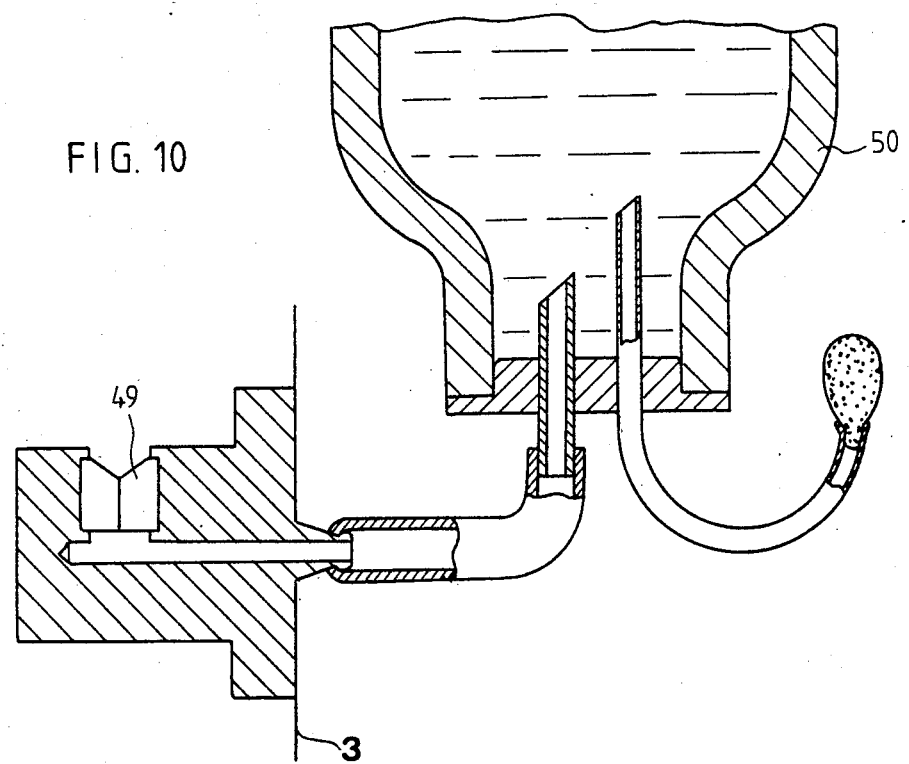

The end of cone 44 is tapered and bevelled, its end most diameter is for example of the order of 2 mm. Two ducts 47 provide the intake for rinsing (sterile water) and sterilizing (high temperature water vapor, formaline, alcohol, etc . . . ) fluids. Discharge takes place in a well 48, formed in the work table of the enclosure, which also serves as housing for the device but also allows external rinsing, sterilizing and drying through rings of holes 39 slanted in the discharge direction. In operation, the handling arm previously places the culture container in the work post. In the simplest case, this latter is only equipped with simple container setting stops (not shown) for placing all the containers in the same position within a millimeter. In this case, the handling arm provides both placing of the box, and the movements of the suction device and of the injection device, if they are separate. It should be noted in this connection that the suction device may also serve for injection as is shown in FIG. 10. The device allows cone 44 to be connected to a liquid supply source through a self closing connection 49 made from a flexible material, particularly from elastomer. Cone 44, by penetrating into this self closure connection, moves aside the initially united internal walls of the flexible material and the end of the cone comes into contact with a liquid to be sucked up. The device of FIG. 10 also comprises an isotherm plug which is connected to the reservoir 50 placed in a cold environment at 4° C. and is placed outside the enclosure shown in FIG. 1, whereas connection 49 is subjected to the sterile laminarflow existing inside this enclosure, so that contamination cannot occur on the residual traces of the nutritive medium.

The complete cycle for changing the medium is as follows. The deposited and centered recipient has no lid (in the case of a very simple organization of the enclosure with said shelving, the lid may exist and must then be removed by the handling arm). The handling arm B grips the injection device previously rinsed (and, if possible, dried by injection of air or dry vapor) and places it in the housing of the container corresponding to the program of the processor, motor 41 is actuated and drives piston 43 upwardly; membrane 45 is depressed in the same direction and transmits the suction to cone 44. The volume sucked up, of the order of a milliliter, never comes into contact with the piston 43. Cone 44 is raised and replaced in well 48, piston 43 is driven downwardly and drives the liquid in front of it. An injection of water through duct 47 rinses the inside of the cone. An air or dry vapor jet, still introduced through duct 47, sterilizes the inside of this cone 44 whose outer part is also subjected simultaneously to the same treatment through the orifices in well 48.

Figure 8:
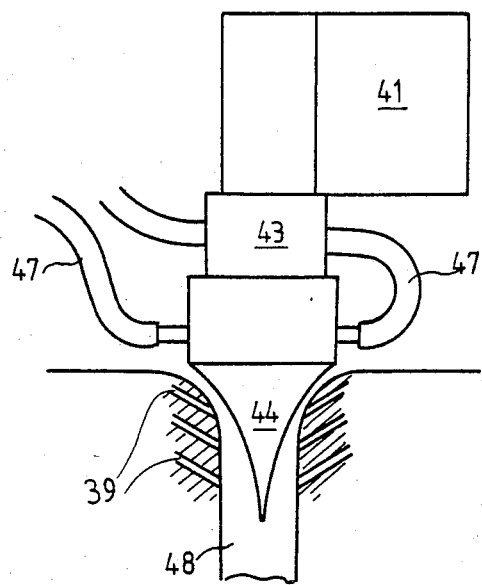
FIGS. 8 to 10 show the suction/injection device for the nutritive medium in accordance with the invention.
Figure 9:
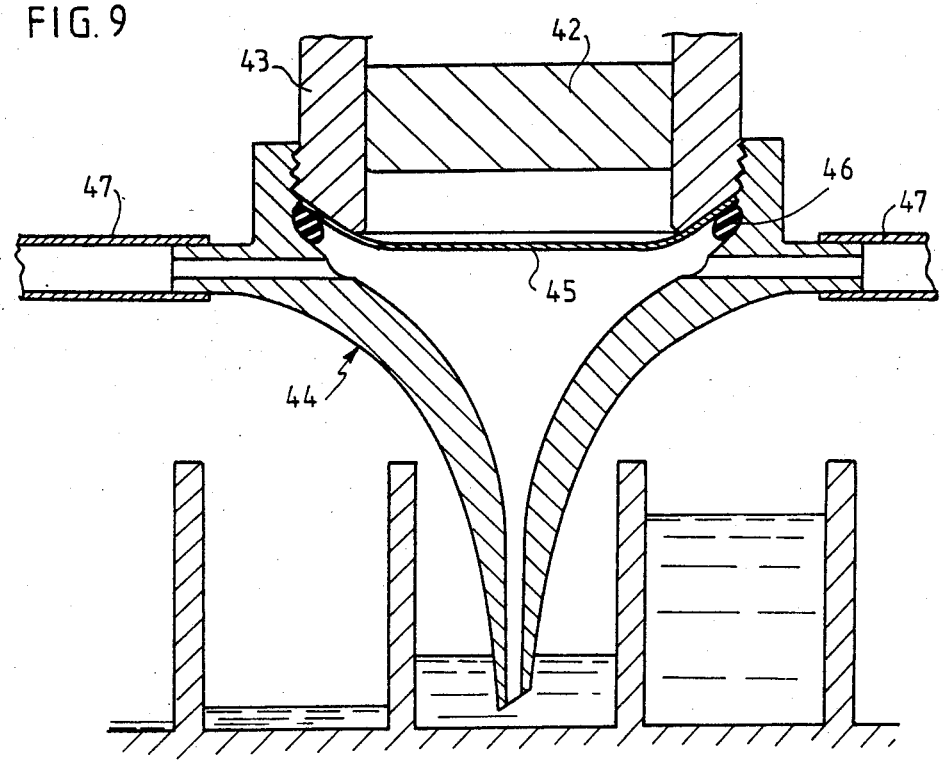

As already mentioned, the injection of fresh medium may be provided by the same suction and injection device shown in FIGS. 8 and 9 connected to the supply device shown in FIG. 10.

It will be readily understood that thus different liquids may be injected, which makes this system very modular.

Figure 11:
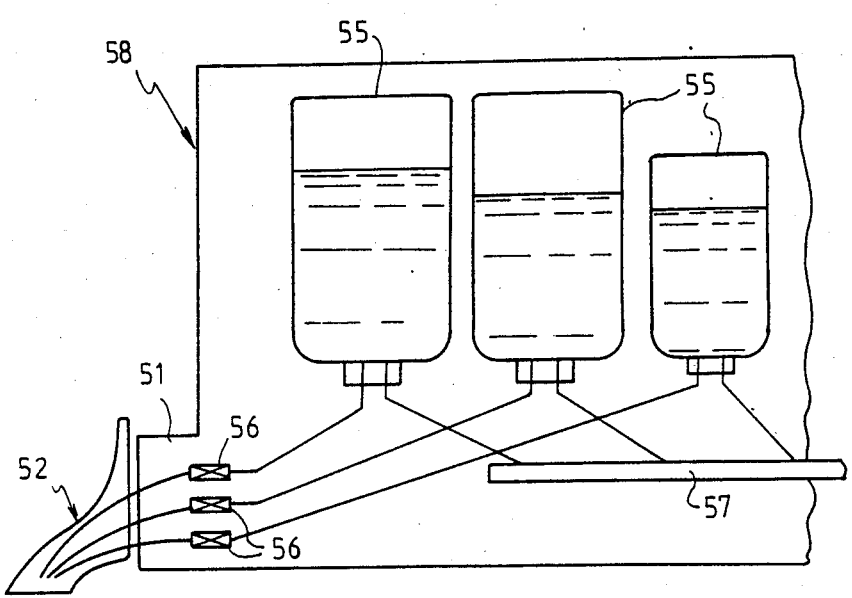
FIGS. 11 and 12 show the fresh nutritive medium injection device intended to cooperate with the device shown in FIGS. 8 and 9 used as a suction device only (namely, without cooperating with the liquid supply device of FIG. 10).
Figure 12:
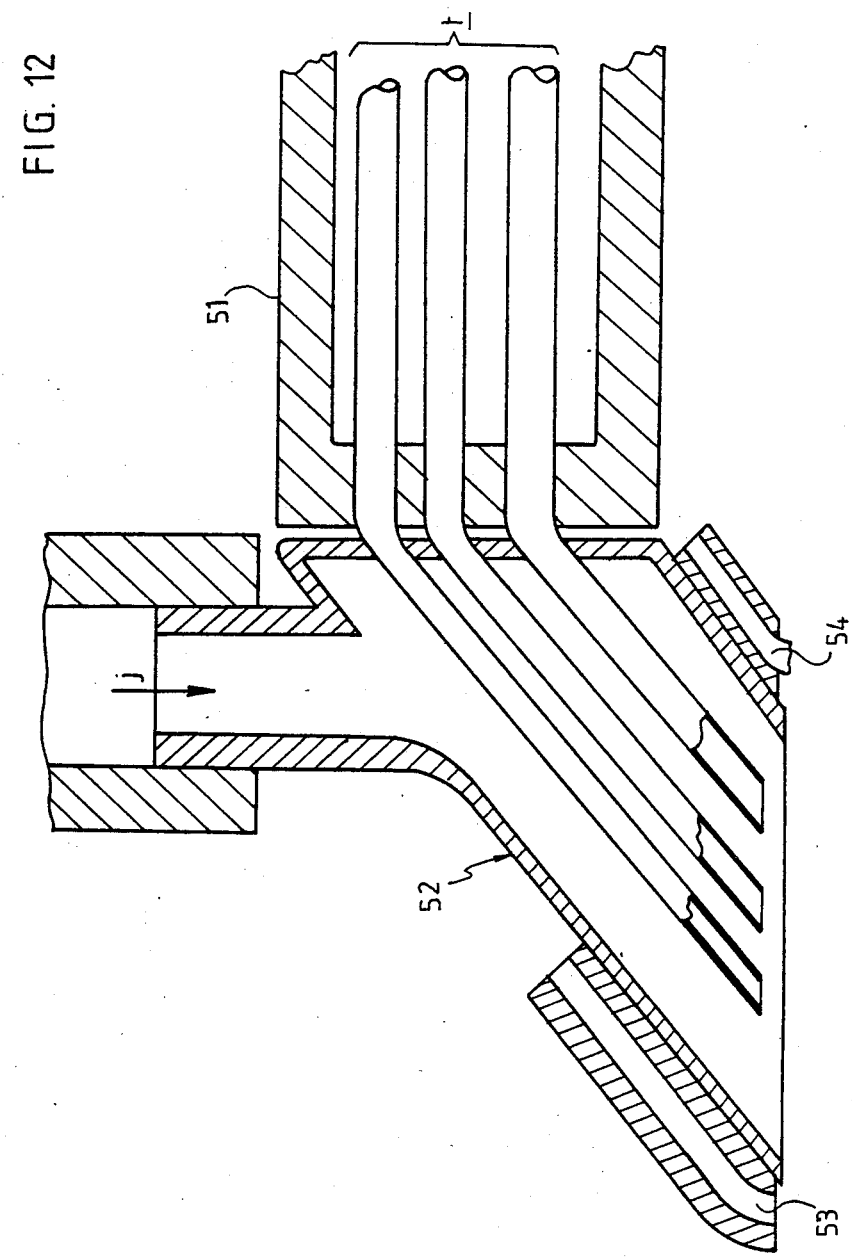

In other cases, it is more advantageous to dissociate the suction and injection functions in particular for saving time and reducing the risks of disseminating contamination which might be created by using a single device. For this, FIGS. 11 and 12 show an injection device comprising an intake of liquids conveyed by one or more metal pipes T, for example six, sheathed in an isotherm duct 51. At 52 has been shown an anticontamination protection sheath which conveys a permanent air jet j at low pressure which prevents the reflux of particles brought into contact with the pipes by possible swirls. The slant given to pipes t allows the flow to be directed against the walls of the cell housings and avoids direct impact against the adherent cells at the bottom of each housing. Optical fibers 53 and 54, directed towards the surface, allow the rise in level to be detected by means of a contactless process.

The previously emptied housings and this injection device may be placed in relation with each other either by the handling arm B, transporting the injection device which has been made mobile, or by moving the box under this device which is made immobile. It is also easy to couple the suction devices of FIGS. 8 and 9 to the injection device of FIGS. 11 and 12. The bottles 55 containing the products to be injected may be connected to sterilizable valve systems 56, with on or off operation, operating for example by crushing elastomer supply pipes. A low pressure sterile air intake 57 pressurizes, in a way known per se, bottles 55 inside the cooled enclosure 58. In operation, the culture container moved by the handling arm B places a given housing under the injection device, the valve or the valves 56 corresponding to the program open, the housing is filled and, as soon as the fixed level is reached, the valve or valves 56 are closed again.

As is clear from what has gone before, the invention is in no wise limited to those of its embodiments and modes of application which have just been described more explicitly; it embraces, on the contrary, all the variants which may occur to a technician skilled in the matter, without departing from the scope or spirit of the present invention.

I claim:

1. A modular apparatus for cell culture, comprising in the same sealed enclosure (2) with isotherms walls (3):
   at least one device (1, R, E) for storing culture containers and further comprising a plurality of modules forming shelving (R) provided with selaed compartments (16) containing said culture containers (4a);
   a temperature regulation device (7);
   a closed circuit laminar flow sterilization device (11, 12, 13, 14), including a filter which sterilizes gas flow by removing microbes;
   a device for supplying and regulating respiratory gases, said enclosure containing at least one additional device for carrying out a cell culture operation and defining a modular workpost in addition to the modular post corresponding to said storage device (1, R, E), the sealed enclosure also containing at least one automatic and programmable arm (B) which is provided with a handling gripper (21) and which carries out all cell culutre operations corresponding to each of the work posts, and comprising a microprocessor for controlling all cell culture operations.

2. Apparatus according to claim 1, wherein gas is supplied for each compartment automatically by means of said arm (B) which sucks up the gas to be renewed, allowing the composition thereof to be analyzed, and which injects renewal gas through a system having two valves (30) formed in the handle (20) of the closure lid (18a) of each compartment (16) and having two ducts communicating with an injection duct (27a) and a suction duct (27b), respectively, carried by the arm (b) and activated wheh the gripper (21) of the arm (b) grips the handle (20) of the lid (16).

3. Apparatus according to claim 1, characterized in that each compartment (16) is held in position by means of a non return rod (25) coming in between a wall of the shelving module (R) and a wall of the compartment itself.

4. Apparatus according to claim 1, characterized in that the connection between adjacent shelving modules (R) takes place through vertical bars (26), particularly in the shape of a T, which are provided with engagement studs (27) penetrating into corresponding housings (28) formed in lateral wings (29) projecting from the vertical rear sides of each shelving module (R).

5. Apparatus according to claim 1 wherein the storage device comprises a plurality of modules forming incubators (E) with isotherm walls and sealed compartments (16a) and comprising:
   a first zone (A), disposed in a front part of said sealed enclosure, assembling together the culture containers in said compartments (16a),
   a second zone (B) disposed in a median part of said sealed enclosure assembling together connections between each compartment (16a) and gas supply sources, and
   a third zone (C) disposed in a rear part of said sealed enclosure, assembling together gas supply devices, regulation devices and filters.

6. Apparatus according to claim 5, wherein said compartments (16a) are provided with a flange on their front face and are fixed to a plate (37) provided with openings (38), disposed in vertical rows, the gas supply for each compartment (16a) being provided automatically by means of ball studs allowing supply valves to open when the compartments are closed (16a), whereas opening of these compartments (16a) deactivates the supply valves.

7. Apparatus according to claim 6, wherein the culture containers are fixed to the lids of the compartments (16a) which thus form drawer boxes (40) for cooperating with with said studs to activate the gas supply when the drawer boxes (40) are introduced into said compartments (16a).

8. Apparatus according to claim 5, wherein said gas supply devices converge in a mixing chamber in which air, $CO_2$ and water vapor content is regulated by means of regulation devices (34, 35, 36), in which chamber slides a piston (33) directing a mixture of of gases from said gas supply devices to a selected compartment (16a).

9. Apparatus according to claim 1, wherein said sealed compartment (16) containing said culture containers (4a) is closed by means of slightly conical lids (18, 18a) equipped with a handle (20) and O-seals.

10. Apparatus according to claim 1, wherein each compartment (16) is transparent and an appropriate space is formed above and below each compartment for introducing, by means of said handling arm (B), a device for carrying out optical measurements.

11. Apparatus according to claim 1, wherein said additional device comprises a device for supplying enriched nutritive medium and removing the impoverished medium.

12. Apparatus according to claim 11 wherein said impoverished nutritive medium removal device comprises a suction device including a stepped mechanical system, a piston (42) in a cylinder (43) threaded at its lower base, about which is screwed a suction cone (44) with tapered and bevelled end, a membrane (45) being clamped between this cone (44) and the base of said cylinder (43) and supported and sealed by an O-seal (46).

13. Apparatus according to claim 12, wherein the cone (44) is connected to two ducts (47) conveying fluids for rinsing and sterilizing the internal part of the cone (44) after the suction and impoverished medium removal operation.

14. Apparatus according to claim 13, wherein removal of the aspirated medium takes place in a well (48) formed in the work table (6) of said enclosure, which well (48) serves also as housing for the suction device and is provided with a series of rings of ducts (39), staggered and slanted in the removal direction for external rinsing, sterilization and drying.

15. Apparatus according to claim 12, wherein said suction device cooperates with a liquid supply device provided with a self closing connection (49) made from a flexible material and subjected to the laminar flow existing inside the enclosure in which said suction cone (44) is introduced whereas a supply reservoir (50) is disposed outside the enclosure and in a cold environment, injection of the fresh or enriched liquid nutritive medium being provided by reversing the action of said stepped micrometer (41).

16. Apparatus according to claim 12, wherein injection of the enriched nutritive medium takes place by means of an injection device which is independent of said suction device and which comprises flasks (55) containing the liquids to be injected inside a cooling block (58), these liquids being conveyed by one or more pipes (t) gathered together in bundles and surrounded by an isotherm sheath (51) projecting from the base of the cooling block (58), the flow rate of each supply pipe (t) being controlled by a sterilizable on/off valve (56).

17. Apparatus according to claim 16, wherein an end part of the bundle of pipes (t) is provided with an anticontamination protection sheath (52) in which is fed a permanent low pressure air jet (j) which prevents the reflux of liquid particles, this anticontamination sheath (52) and the ends of said supply pipes (t) being slanted so as to direct injection liquid against a wall of said culture containers and to avoid direct impact against the cells which adhere to the bottom of each container.

18. Apparatus according to claim 1, wherein said additional device comprises a device for rinsing and sterilizing the containers.

19. Apparatus according to claim 1, wherein said additional device comprises a device for distributing nutritive media.

20. Apparatus according to claim 1, wherein said additional device comprises a device for distributing pharmacological substances.

21. Apparatus according to claim 1, wherein said additional device comprises a cell distribution device.

22. Apparatus according to claim 1, wherein said additional device comprises at least one monitoring means for detecting changes in cell culture conditions.

23. Apparatus according to claim 22, wherein said monitoring means is coupled to a motor driven stage.

24. Apparatus according to claim 23 wherein said monitoring means is coupled to a means for analyzing information received therefrom.

25. Apparatus according to claim 1, wherein said additional device comprises means for physically or chemically analyzing cell cultures.

26. Apparatus according to claim 1, wherein said additional device comprises transplanting means.

27. Apparatus according to claim 1, wherein said additional device comprises storage means.

28. Apparatus according to claim 1, wherein said additional device comprises means for spraying.

29. Apparatus according to claim 1 further comprising a device for collecting liquids accidently spilled in a work post, including a single funnel placed below the work table which is provided with a lateral orifice for communication with the laminar flow sterilization circuit.

* * * * *